(12) United States Patent
Shirai et al.

(10) Patent No.: US 7,061,619 B2
(45) Date of Patent: Jun. 13, 2006

(54) CHEMICAL SUBSTANCE MEASURING APPARATUS USING OPTICAL WAVEGUIDES

(75) Inventors: Masataka Shirai, Higashimurayama (JP); Toshiki Sugawara, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 238 days.

(21) Appl. No.: 10/751,489

(22) Filed: Jan. 6, 2004

(65) Prior Publication Data

US 2004/0239944 A1    Dec. 2, 2004

(30) Foreign Application Priority Data

May 27, 2003    (JP)    ............................ 2003-148870

(51) Int. Cl.
*G01B 9/02*    (2006.01)
(52) U.S. Cl. .................... 356/481; 356/477; 485/12
(58) Field of Classification Search ................ 356/517, 356/477, 481, 480; 250/227.19, 227.27
See application file for complete search history.

(56) References Cited

U.S. PATENT DOCUMENTS

| 5,485,277 A | * | 1/1996 | Foster ........................ 356/445 |
| 5,710,630 A | * | 1/1998 | Essenpreis et al. ......... 356/479 |
| 6,429,023 B1 | | 8/2002 | Gharavi |

OTHER PUBLICATIONS

Biacore 2000, Product Information, "High Sensitivity Automated Analysis System", Dec. 2001, 2 pages.

Biacore 3000, Product Information, "The High Performance Research System", Mar. 2003, 12 pages.

The Electronic Toolbox, Part 1, Analytical Chemistry, vol. 57 (Sep. 1985), edited by Raymond E. Dessy, pp. 1188A-1202A.

L.M. Lechuga, A.T.M. Lenferink, R.P.H. Kooyman and J. Greve, "Feasibility of Evanescent Wave interferometer Immunosensors for Pesticide Detection: Chemical Aspects", 1995 Elsevier Science S.A., Sensors and Actuators B24-25, 1995 Elsevier Science SA, pp. 762-765.

* cited by examiner

*Primary Examiner*—Gregory Toatley
*Assistant Examiner*—M J Detschel
(74) *Attorney, Agent, or Firm*—Reed Smith LLP; Stanley P. Fisher, Esq.; Juan Carlos A. Marquez, Esq.

(57) ABSTRACT

A chemical substance detection sensor for improving detection stability, resistance to vibration, compactness, and sensitivity, wherein said sensor is comprised of optical waveguides for dividing and propagating light from a wavelength-tunable light source, a chamber for allowing a sample to flow through regions of two optical waveguides including ligands provided on one of the two optical waveguides, an optical combiner/splitter for combining and redividing the outputs from the two optical waveguides, and a detector for detecting a chemical substance contained in the sample under test by capturing the interference light output from the optical combiner/splitter. The operating point of this chemical substance detection sensor is adjusted by controlling the wavelength of the light source so as to equalize the outputs of two detectors separated by the optical combiner/splitter when the reference sample not containing the substance for detection flows into the chamber.

20 Claims, 12 Drawing Sheets

CHEMICAL SUBSTANCE MEASURING APPARATUS USING OPTICAL WAVEGUIDES

PRIORITY CLAIM

This application claims priority under 35 U.S.C §119 to Japanese patent application P2003-148870 filed May 27, 2003, the entire disclosure of which is hereby incorporated by reference.

FIELDS OF THE INVENTION

The present invention relates to a chemical substance detector using optical waveguides and also relates to a chemical substance measuring apparatus using a chemical substance detector. More specifically, the present invention relates to a chemical substance and biological substance detector and measuring apparatus for detecting toxic chemical substances and harmful pathogenic germs generated in industrial plants, toxic chemical substances and harmful microorganisms present in the environment, and proteins and pathogenic germs relating to disease and healthcare at home or in hospitals.

BACKGROUND OF THE INVENTION

Various chemical substance detection apparatus have been used up until now in extremely diverse fields including the environmental fields medical treatment, food industry, and pharmaceutical industry. Those apparatuses were designed to detect the intensity of interactions between proteins in living organisms, to detect concentrations of proteins or other chemical substances in living organisms, and to detect environmental or chemical substances by utilizing fluorescent materials or fluorescent labels. Among these, the method using fluorescent materials of course utilizes the fluorescence reactions that occur through direct or indirect binding of fluorescent materials to the chemical substance for detection. This method has the disadvantage that reactions with fluorescent materials must constantly continue during detection and monitoring of a particular chemical substance. This also creates a resultant problem that chemical substances containing fluorescent materials flow downstream of the chemical substance being detected.

A chemical substance detector that measures the quantity of chemical substances without using fluorescent labels is described in, http://www.biacore.co.jp, Analytical Chemistry vol. 57, pp. 1188A (1985). In this chemical substance detector, a chemical substance (ligand), which specifically binds to the chemical substance to be detected, is fixed on a substrate in order to measure whether the chemical substance to be detected binds to the ligand. This chemical substance detector is also capable of measuring changes over time in the binding interaction between the chemical substance to be detected and the ligand. Furthermore, this detector is capable of measuring the extent (probability) of how strongly a chemical substance binds to another substance. These types of chemical substance detection methods utilize the binding between the chemical substance fixed on a substrate and the chemical substance to be detected. Among these are methods of the known art that detect changes in the refractive index in the vicinity of the substrate surface which occur when the chemical substance to be detected is bound and adsorbed to the chemical substance fixed on the substrate.

Among the above-mentioned methods for detecting changes in the refractive index in the vicinity of the substrate surface, two methods are known in the related art. One method is a technique utilizing surface plasmon resonance, and the other is a technique for detecting phase changes of light propagating through optical waveguides.

Among the chemical substance detection sensors not using fluorescent labels, measurement apparatus employing a Mach-Zehnder interferometer have the advantage of high detection sensitivity. A chemical substance detection sensor using a Mach-Zehnder interferometer, similar to the structure illustrated in FIG. 1 (top view) and FIG. 2 (sectional view), is described in, Sensors and Actuators B, 24/25 pp. 762 (1995). In this chemical substance detection sensor, light emitted from a fixed-wavelength laser light source 51 is divided into two beams by a beam splitter 52. The divided light beams then enter a slab waveguide 63 formed on a glass substrate 55. This slab waveguide is a thin film formed on the glass substrate and has a refractive index higher than that in the glass substrate and has a thickness smaller than the wavelength of the light propagating through the thin film. In the slab waveguide, the light is confined so as not to propagate in the direction of the cross section, but is not confined in parallel with the substrate surface. The light beams divided by the beam splitter 52 respectively propagate along optical paths 53 and 54 through the slab waveguide. One light beam in the optical path 53 propagates through a region 56 where ligands 66 are fixed on the surface to specifically adsorb a chemical substance 64 to be detected. The other light beam in the optical path 54 propagates through a region 57 where the substance to be detected is not adsorbed. These two light beams are then combined and redivided by an optical coupler 58 in which interference of the two light beams occurs. The intensity of each light beam after causing the interference is then measured respectively with photodetectors 60 and 61 as the outputs changing in accordance with the phase difference between the optical paths. At this point, the phase of the light passing through the optical waveguide 53 changes in proportion to the adsorbed amount of the chemical substance to be detected, causing changes in the output difference between the photodetectors 60 and 61. These changes are caused because as shown in FIG. 2, the distribution of each light propagating through the optical paths 53 and 54 spreads out of the slab waveguide thin film 67 and when the chemical substance to be detected binds to the ligands 66, the refractive index of the light propagating through the optical path 53 changes in proportion to the adsorbed amount. Moreover, the amount of change in the phase of the light passing through the region 56, which is caused by the change in the refractive index, becomes larger than the amount of change in the phase of the light passing through the region 57. Based on this principle, the concentration of the chemical substance to be detected can be measured. The adsorbed amount of a particular chemical substance can in this way be measured by using a Mach-Zehnder interferometer.

As shown in FIG. 3, the intensities of the light after being divided and then detected with the photodetectors 60 (shown as PD1 output) and 61 (shown as PD 2 output) actually change along a trigonometric function curve, and the difference between them also changes along a trigonometric function curve. By making the phase change correspond to the abscissa of this intensity change graph and by also making the phase change correspond to the adsorbed amount of a substance, the concentration of the particular chemical substance can be measured. At this time, the relation between the amount of the phase change and the adsorbed amount of the substance is determined by measuring the phase change of the substance to be detected whose concentration is known beforehand.

The following documents disclose the related art of the present invention.

SUMMARY OF THE INVENTION

As can be seen from the graph of FIG. 3, the difference in intensity between the two divided light beams changes most significantly at a point where the intensities of the two light beams are equal. However, that point shifts from where the intensities of the two light beams are equal, because of factors such as the optical coupler that combines and redivides the light tends to shift away from the ideal position, the asymmetrical arrangement of the slab waveguide, and the chemical substance adsorption on the slab waveguide. This means that optimal sensitivity for the chemical substance to be detected cannot be constantly maintained. To solve this problem, the prior art techniques use an optical phase plate 59 as shown in FIG. 1, which rotates to adjust the phase difference between the two light beams before they combine, in order to fix the phase difference at a point where the intensities of the two light beams after being combined and redivided are equal. In other words, the phase difference is fixed at the operating point shown in FIG. 3. However, this example requires mechanically moving parts for rotating the phase plate and therefore must use so-called "bulk optics" 1, that make the apparatus larger in size. Moreover, this type of apparatus has further disadvantages such as a lower resistance to vibration.

U.S. Pat. No. 6,429,023 B1 discloses a technique that does not have mechanically movable parts. This technique instead uses materials (particularly polymer materials) having electro-optic effects as the materials for the optical waveguides in order to constantly maintain maximum sensitivity during measurement. With this technique, the phase difference between the two light beams is changed by the application of a voltage to one polymer waveguide (for example 54) so as to compensate for the shifted phase and thus the intensities of the redivided light beams are maintained at the same level. However, with this technique, the amount of phase shift in the materials having electro-optic effects changes over time, making it difficult to maintain a constant amount of phase shift over extended periods of time. This technique therefore still has a problem with long term measurement stability.

Accordingly, the present invention may achieve a chemical substance detection sensor capable of high sensitivity measurements by maintaining the conditions of the maximum sensitivity, while improving the compactness, resistance to vibration, and long term stability, as well as to achieve a chemical substance measuring apparatus using the chemical substance detection sensor.

To achieve the above-mentioned, a chemical substance detection sensor of the present invention comprises:

two optical waveguides for dividing and transmitting light emitted from a light source;

a reaction chamber for allowing a sample to flow through the regions of the two optical waveguides including ligands provided on one of the two optical waveguides;

an optical combiner/splitter for combining and redividing the outputs from the first and second optical waveguides; and a detector for measuring the intensities of the two output light beams from the optical combiner/splitter, wherein the optical path lengths of the first and second optical waveguides differ from each other by ¼ or more of a wavelength, adjusts without bulk optics, the relative phase difference between the light beams from the light source propagating though the optical paths of the first and second optical waveguides.

Preferred embodiments and modes of the above-mentioned optical phase adjustment include examples using a wavelength-tunable semiconductor laser as the light source, or using a fixed-wavelength light source combined with a device capable of adjusting the wavelength of the output light of the light source, or using a temperature controller for regulating the temperatures on the optical paths of the first and second waveguides.

The chemical substance measuring apparatus of the present invention uses the above-mentioned chemical substance detection sensor of the present invention and comprises:

an output operation controller for processing the output of the chemical substance detection sensor;

a flow controller for controlling the flows of the reference sample and sample under test into the reaction chamber;

a temperature controller for controlling the temperature in the reaction chamber; and a measurement controller for controlling the flow controller, temperature controller, and output operation controller.

The phase adjustment apparatus has an adjustment mode in which the wavelength of the light source or the temperature of the optical waveguides (reaction chamber) is adjusted so as to set the operating point where the output of the sensor becomes 0 (zero) when measuring the reference sample such as pure water not containing the substance to be detected, and the wavelength of the light source used to set the operating point is maintained.

According to the chemical substance detection sensor of the present invention, if, for example, the difference between the optical path lengths of the first and second waveguides is $\Delta l$, the amount of the optical phase shift corresponding to this $\Delta l$ can be adjusted by changing the wavelength. More specifically, if the wavelength changes from $\lambda$ to $\lambda+\Delta\lambda$, then the phase difference between the two light beams before they are combined changes from $2\pi(\Delta l/\lambda)$ to $2\pi(\Delta l/(\lambda+\Delta\lambda))$. By making use of this fact, the phase difference is appropriately adjusted during setting of the operating point and fixed at a state where the intensities of the two light beams after being combined and redivided become equal. In other words, the phase difference is fixed at the operating point shown in FIG. 3. Based on this condition, the phase difference corresponding to the adsorbed amount of the substance to be detected, or the concentration of the substance, is found. The wavelength change $\Delta\lambda$ is achieved by changing the wavelength of the light source or by changing the temperature in the reaction chamber.

The chemical substance measuring apparatus of the present invention may be used in the following cases. These cases include:

finding the amount of the detected substance directly from the output of the above-mentioned chemical substance detection sensor during detection of the sample under test, while maintaining the wavelength of the light source used to fix the operating point;

finding the amount of the detected substance from the wavelength difference between the light source wavelengths when fixed and when adjusted during detection of the sample under test while controlling the wavelength of the light source even during detection of the sample under test, so that the output from the chemical substance detection sensor becomes 0 (zero); and finding the amount of the detected substance from the temperature difference between the temperatures when the operating point was first set and when it was adjusted during detection of the sample under test, while using a fixed-wavelength light source and controlling the temperature in the reaction chamber during setting of the operating point and also during detection of the sample under test, so that the output from the chemical substance detection sensor reaches 0 (zero).

Accordingly, the operating point setting for the chemical substance detection sensor can be changed by controlling the wavelength of the light source or the temperature in the reaction chamber, without using bulk optics for phase adjustment. By making use of the fact that the optical path lengths of the two waveguides differ from each other, the phase difference can also be adjusted by the wavelength change and set at the operating point shown in FIG. 3 where the changes in the photodetector outputs are most significant.

DETAILED DESCRIPTION OF THE PREFERRED EMBODIMENTS

The embodiments of the present invention are hereafter described in detail with reference to the drawings.

(First Embodiment)

Figure 4:
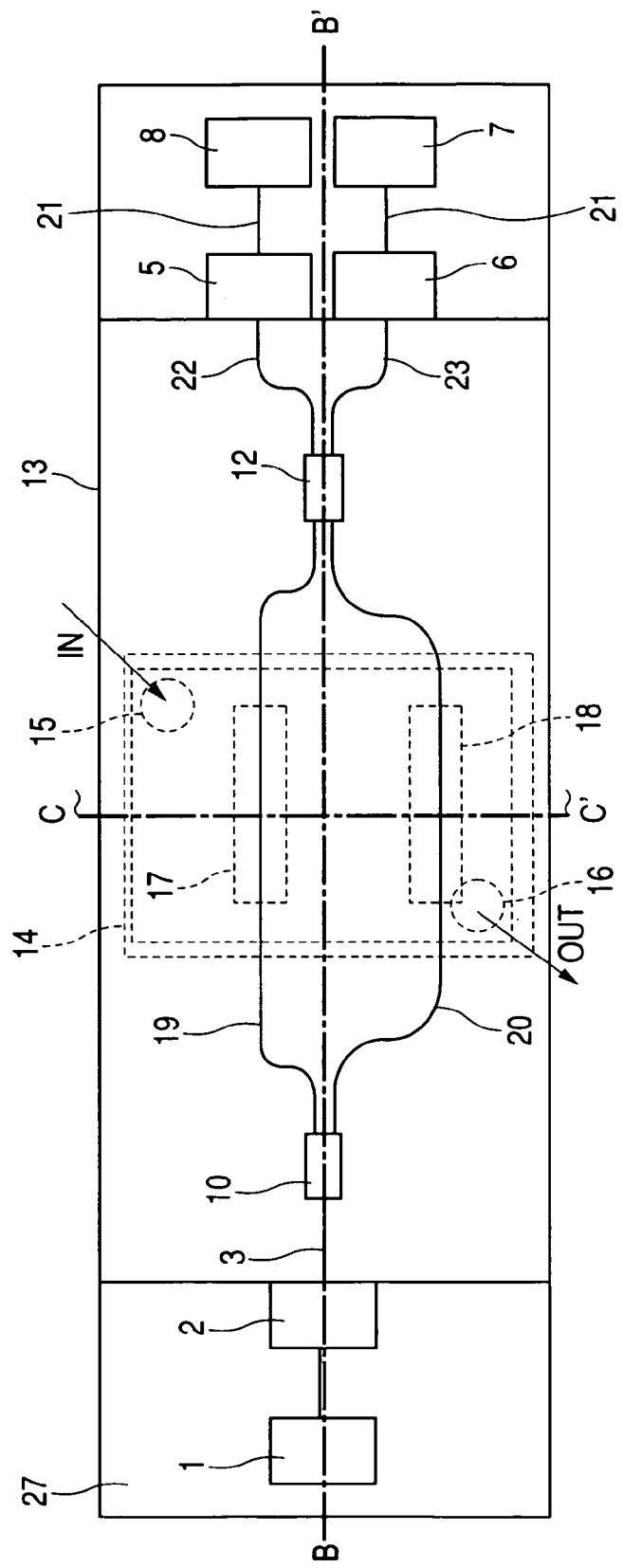
FIG. 4 is a top view showing an embodiment of a chemical substance detection sensor of the present invention.
Figure 5:
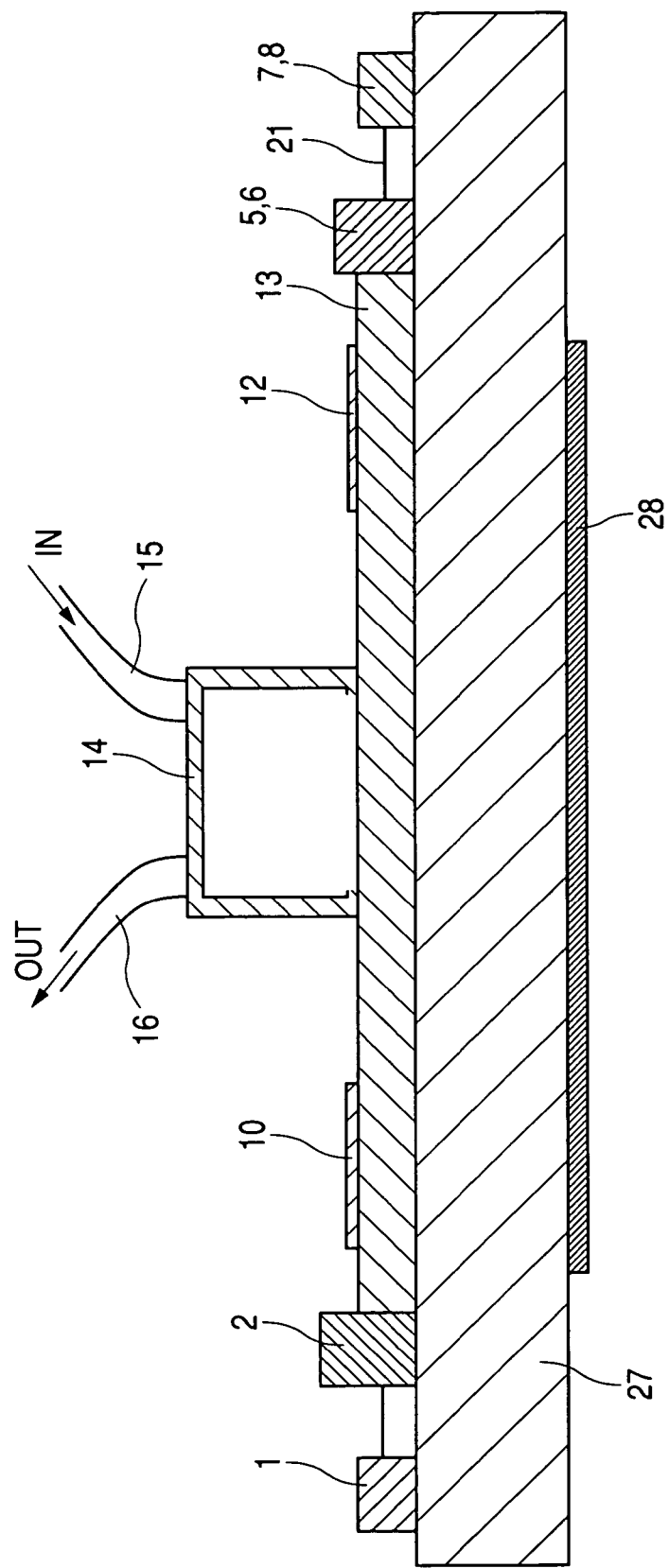
FIG. 5 is a sectional view taken along line C–C' of FIG. 4.
Figure 6:
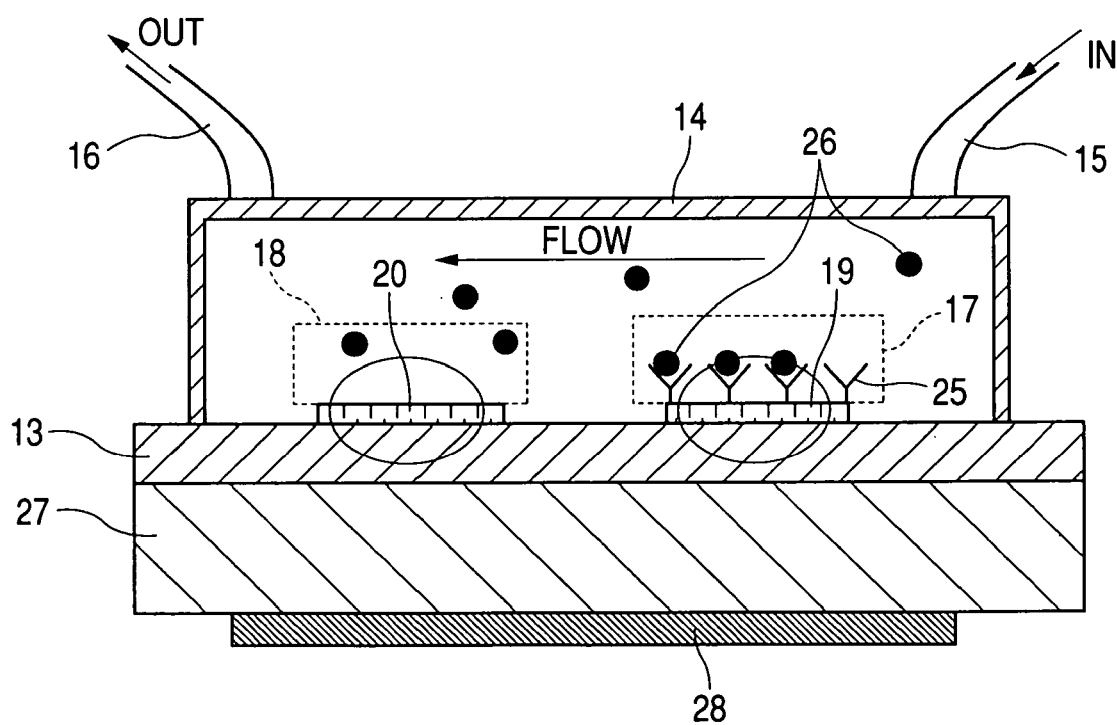
FIG. 6 is a sectional view taken along line B–B' of FIG. 4.
Figure 7:
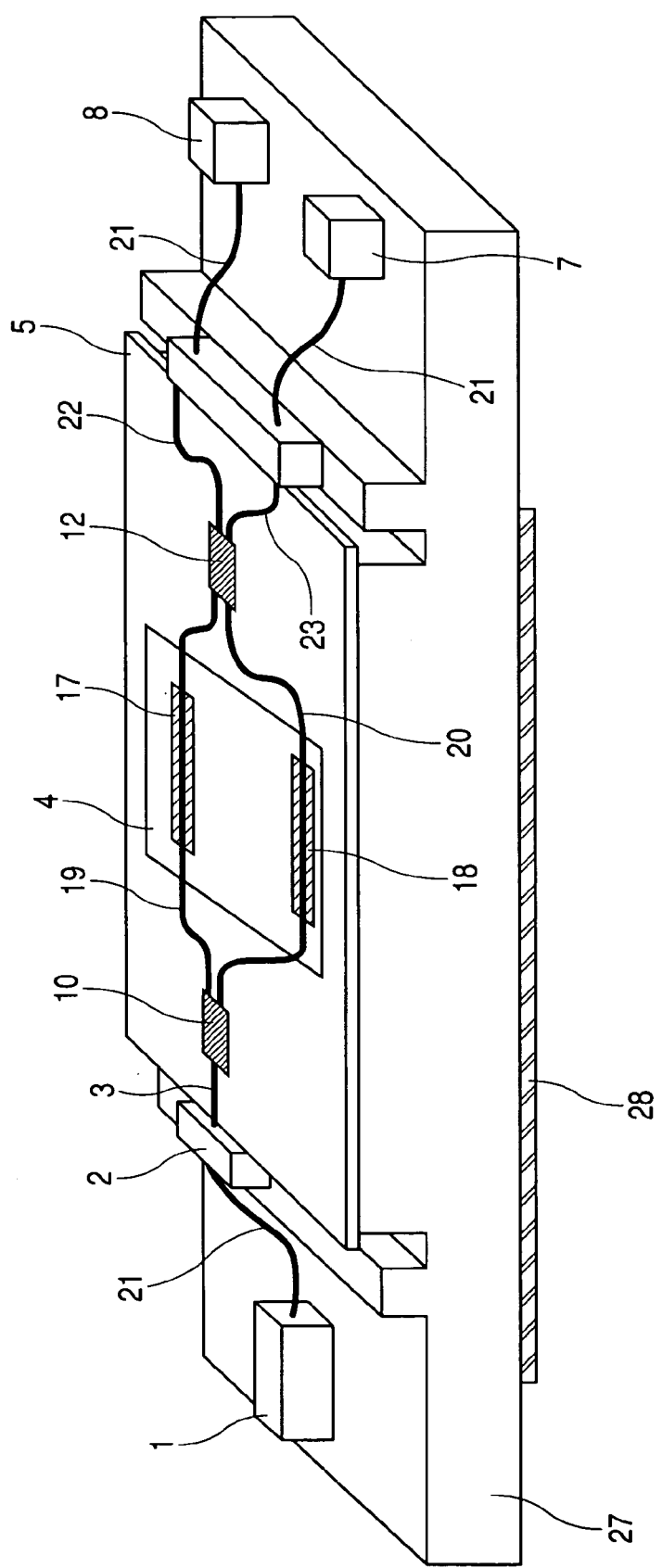
FIG. 7 is a perspective view showing an embodiment of a chemical substance detection sensor of the present invention.

In FIG. 4 through FIG. 7, an example of a chemical substance detection sensor of the present invention is illustrated in different views. FIG. 4 shows a top view. FIG. 5 is a sectional view taken along line C–C' of FIG. 4. FIG. 6 is a sectional view taken along line B–B' of FIG. 4. FIG. 7 is a perspective view.

As illustrated, the optical waveguides 19 and 20 are formed on an optical waveguide substrate 13 installed on a support plate 27, so that their lengths differ from each other. A laser beam emitted from a light source 1 which is a wavelength-tunable laser formed on the support plate 27 is guided into an optical waveguide 3 on an optical waveguide substrate 13 by way of an optical coupling 2 for directing the light beam into the optical waveguide 3. The output from the optical waveguide 3 is divided by an optical splitter 10 formed on the optical waveguide substrate (hereafter also simply called "substrate") 13 and then guided respectively into the optical waveguides 19 and 20.

The output end of the waveguides 19 and 20 is coupled to a combiner/splitter 12 formed on the substrate 13. The combiner/splitter 12 combines the output light from the waveguides 19 and 20 to produce interference and then outputs the interference light to the optical waveguides 22 and 23. The output light of the optical waveguides 22 and 23 respectively enters photodetectors 8 and 7 by way of the optical couplers 5 and 6, and the optical fibers 21. In other words, this configuration constitutes a Mach-Zehnder interferometer.

Figure 8:
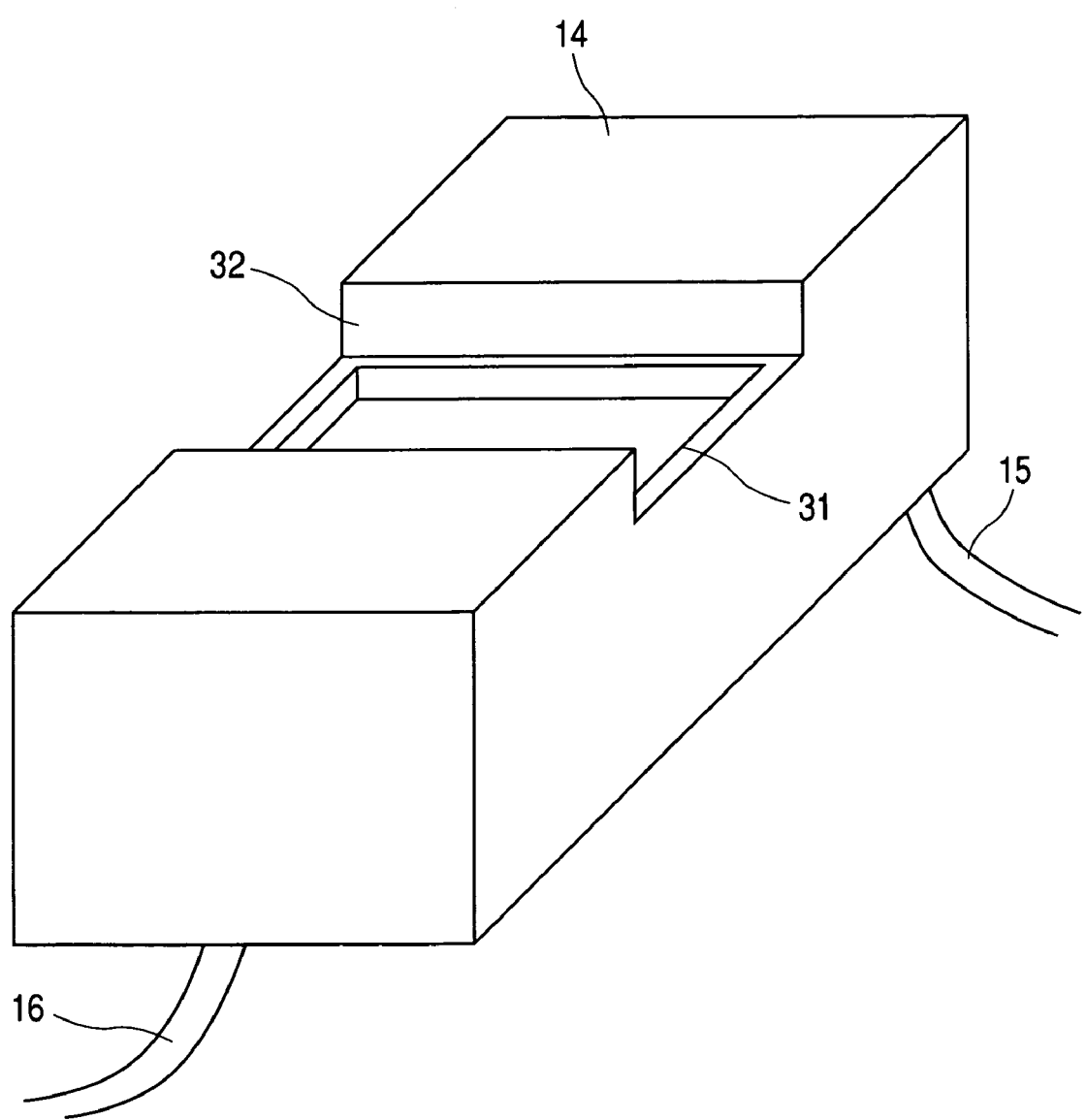
FIG. 8 is a perspective view of the chamber shown in FIG. 5.

A box type enclosure 14 constituting a reaction chamber is arranged to enclose a region 17 of the optical waveguide 19 and a region 18 of the optical waveguide 20. This enclosure 14 is made of Teflon (registered trademark) into a shape shown in the perspective view of FIG. 8. When installing the enclosure 14 onto the optical waveguide substrate 13, a groove 32 provided in the enclosure 14 engages with the substrate 13. A square 4 on the substrate 13 and a square 31 on the enclosure 14 coincide with each other at this point.

The configurations around and inside the enclosure 14 are illustrated in FIG. 5 which is a sectional view taken along line B–B' of FIG. 4 and also in FIG. 6 which is a sectional view taken along line A–A' of FIG. 4. The region 17 is formed on the waveguide 19 installed on the optical waveguide substrate 13. A chemical substance (ligand) specifically binding to the substance to be detected 26 is fixed in this region 17. The substance to be detected however is not adsorbed in the region 18 formed on the optical waveguide 20. The optical waveguide substrate 13 is mounted on the support plate 27. A temperature control plate 28 is installed on the bottom of the support plate 27, or in other words installed on the backside of the support plate 27, where the optical waveguide substrate 13 is not formed. The temperature control plate 28 controls the temperatures of the optical waveguide substrate 13 and the support plate 27, and is used to maintain the thermal equilibrium conditions such as temperatures between the substance to be detected 26 and the ligand 25.

The enclosure 14 has an input port 15 with a pipe for injecting a liquid or gas containing the sample or the substance to be detected. The enclosure 14 also has an output port 16 with a pipe for discharging the sample from inside the enclosure 14. The sample constantly flows through the enclosure 14 by way of the input port 15 and output port 16.

A method for detecting a chemical substance with the above-mentioned chemical substance detection sensor will be described next.

Figure 1:
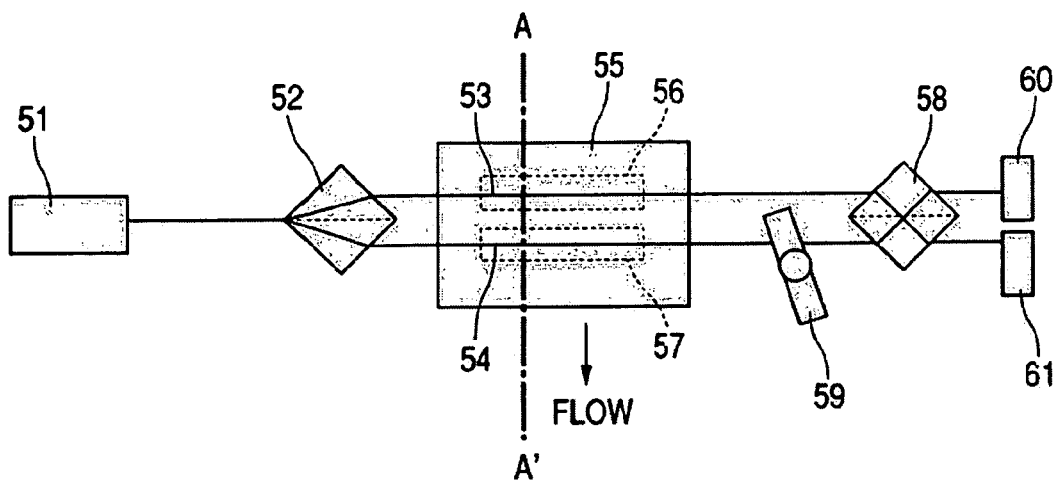
FIG. 1 is a block diagram of a well-known chemical substance detection sensor.
Figure 2:
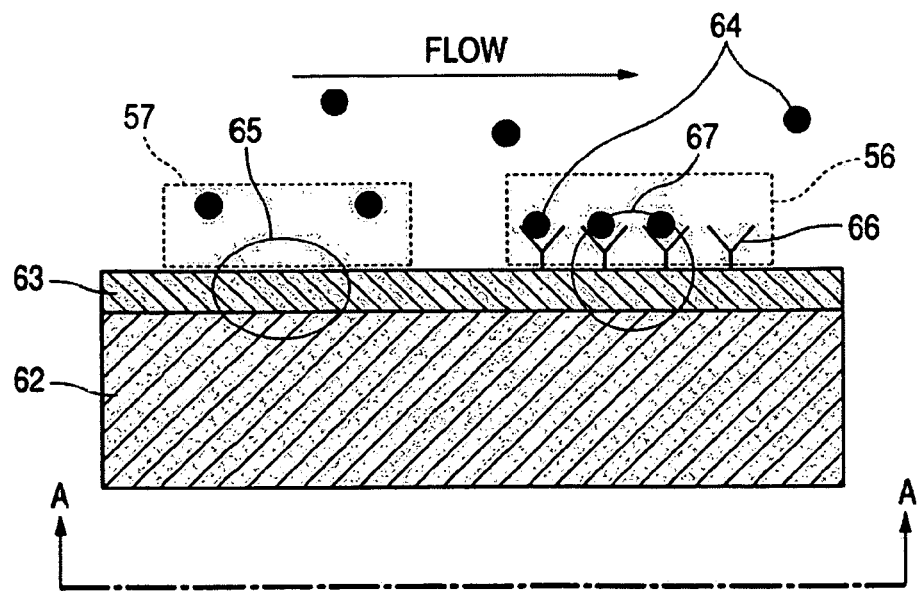
FIG. 2 is a sectional view taken along line A–A' of FIG. 1.
Figure 3:
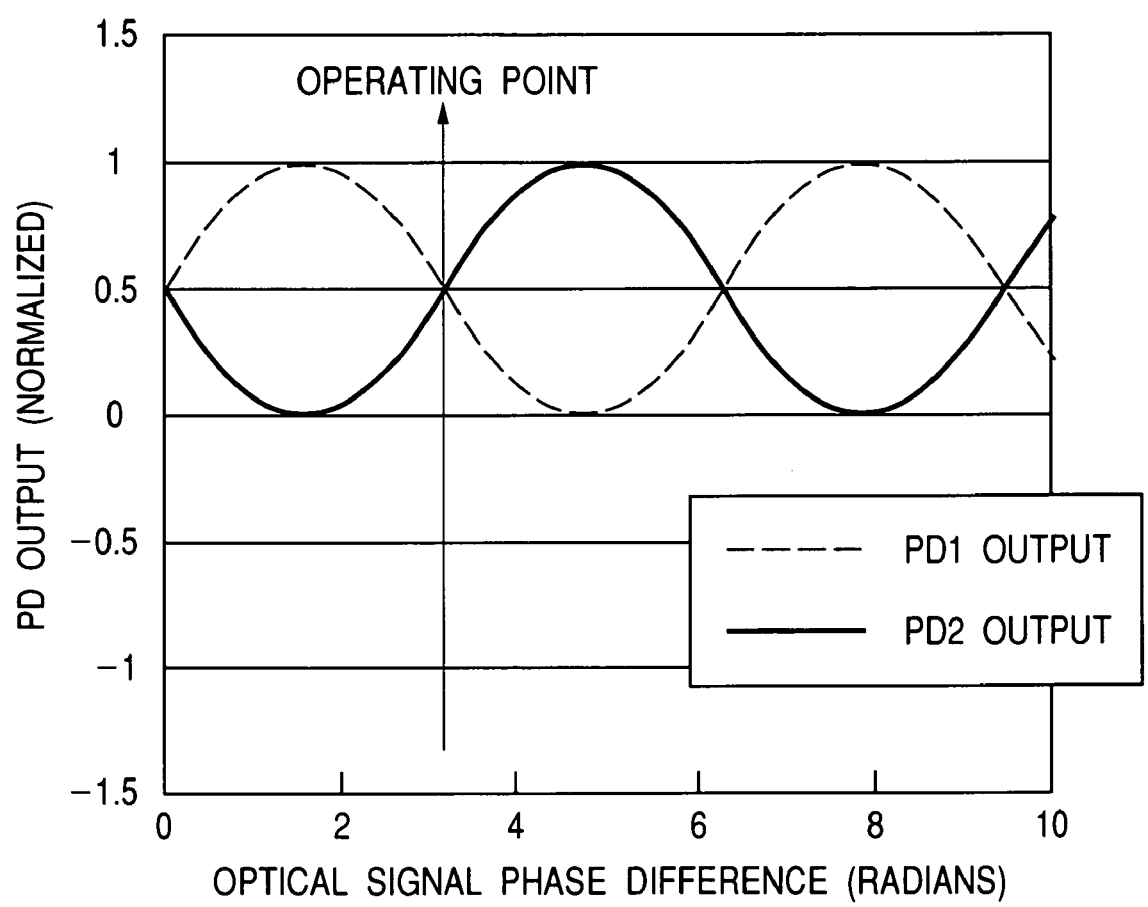
FIG. 3 is a graph showing PD1/PD2 outputs versus optical signal phase difference taken with a Mach-Zehnder interferometer.

In this first embodiment of the present invention, the wavelength of the wavelength-tunable laser is changed by controlling, for example, the voltage for the laser, so the phase difference can be adjusted by the wavelength change without using bulk optics for phase adjustment. The operating point can therefore be adjusted at the point shown in FIG. 3 where changes in the photodetector outputs are most significant. This allows adjusting the phase difference between the light beams propagating through the two optical waveguides without using any mechanically movable parts. In the operating principle of the above-mentioned adjustment, if for example, the difference between the optical path lengths of the two waveguides 19 and 20 is $\Delta 1$, the amount of the optical phase shift corresponding to this length $\Delta 1$ is adjusted by changing the wavelength. More specifically, if the wavelength changes from $\lambda$ to $\lambda+\Delta\lambda$, then the phase difference between the two light beams before they are combined changes from $2\pi(\Delta 1/\lambda)$ to $2\pi(\Delta 1/(\lambda+\Delta\lambda))$. By making use of this fact, the phase difference is appropriately adjusted and fixed at a state (operating point in FIG. 3 which is a most significant and sensitive point for the photodetector outputs) where the intensities of the two light beams after being combined and redivided or the light intensities incident on the photodetectors 8 and 7 become equal when measuring the reference sample that does not contain the substance to be detected. Based on this condition, the phase difference corresponding to the adsorbed amount of the substance to be detected, or, the concentration of the substance, is found. This detection method allows higher stability, improved compactness, and higher resistance to vibration since use of bulk optics is eliminated.

Methods for manufacturing the chemical substance detection sensor of this embodiment are described next.

A silicon substrate with a thickness of 1 millimeter was used as the substrate 13 on which a thermal curing (hardening) polymer (refractive index 1.5) was coated to a thickness of 15 microns in order to form a Mach-Zehnder interferometer. On that polymer coat, another thermal curing polymer (refractive index 1.8) was coated to a thickness of 0.3 microns for use as a core layer for the optical waveguides to be formed. After coating the polymers, a photoresist pattern for defining the optical waveguide pattern was formed and dry etching then carried out so that only the core layer was etched to fabricate optical waveguides with a width of 6 microns. The length of the optical waveguide 19 was fabricated this way to 15,000 microns and the length of the other optical waveguide 20 to 15,080 microns. It was confirmed that light propagating through the two optical waveguides 19 and 20 caused a change in the optical phase shift by $2\pi$ versus a change of approximately 20 nanometers in the wavelength of the light source. The size of the splitter 10 was made 20 microns in width and 310 microns in length, while the size of the combiner/splitter 12 was made to 14.5 microns in width and 395 microns in length. Using these dimensions allowed the typical loss in the Mach-Zehnder interferometer to be limited to 1 dB.

Next, a silane coupling material was applied to the region 17 by using photoresist, in order to fix anti-dioxin monochronal antibody in the region 17, which is used with immunoassay for the purpose of detecting dioxin present in a sample solution. The substrate 13 including the above-mentioned antibody was then immersed in a buffer solution to fix the anti-dioxin monochronal antibody in the region 17. When detecting another substance, an antibody (ligand) applicable for that substance should of course be fixed in the region 17. To improve sensitivity, a secondary antibody may be used that binds to the antibody fixed together with the substance to be detected. Furthermore, the measurement accuracy can of course be enhanced by fixing into the region 18, another antibody in a competitive relation with the antibody fixed in the region 17, although nothing was fixed in the region 18 in this embodiment.

In this embodiment of the present invention, optical fiber blocks were used as an optical coupling from the light source (laser) 1 to the optical waveguide 3, and from the optical waveguides 22 and 23 to the photodetectors 8 and 7. The optical loss in these fiber blocks was relatively large, but this loss level does not deteriorate the sensitivity. Numerals 21, 25, and 26 indicate optical fibers. A 1.55 micron wavelength distributed feedback laser diode was used as the light source 1. A Peltier element was used as the temperature control plate 28. Photodetectors with an InGaAs absorption layer were used as the photodetectors 8 and 7. To minimize the sensitivity variations between the photodetectors 8 and 7, planar elements with a thick absorption layer thicker than 1 micron were used. The light source (laser) 1, substrate 13, and photodetectors 8 and 7 were arranged on the support plate 27 made of copper with a high thermal conductivity, and the temperature of the support plate 27 was controlled by the Peltier element 28 so as to maintain the substrate at a constant temperature.

We manufactured the dioxin detector apparatus as described above. With this apparatus, we succeeded in detecting minute changes equivalent to a change of $10^{-7}$ in the refractive index, making it possible to perform sub-PPB level measurements using a secondary antibody.

(Second Embodiment)

Figure 9:
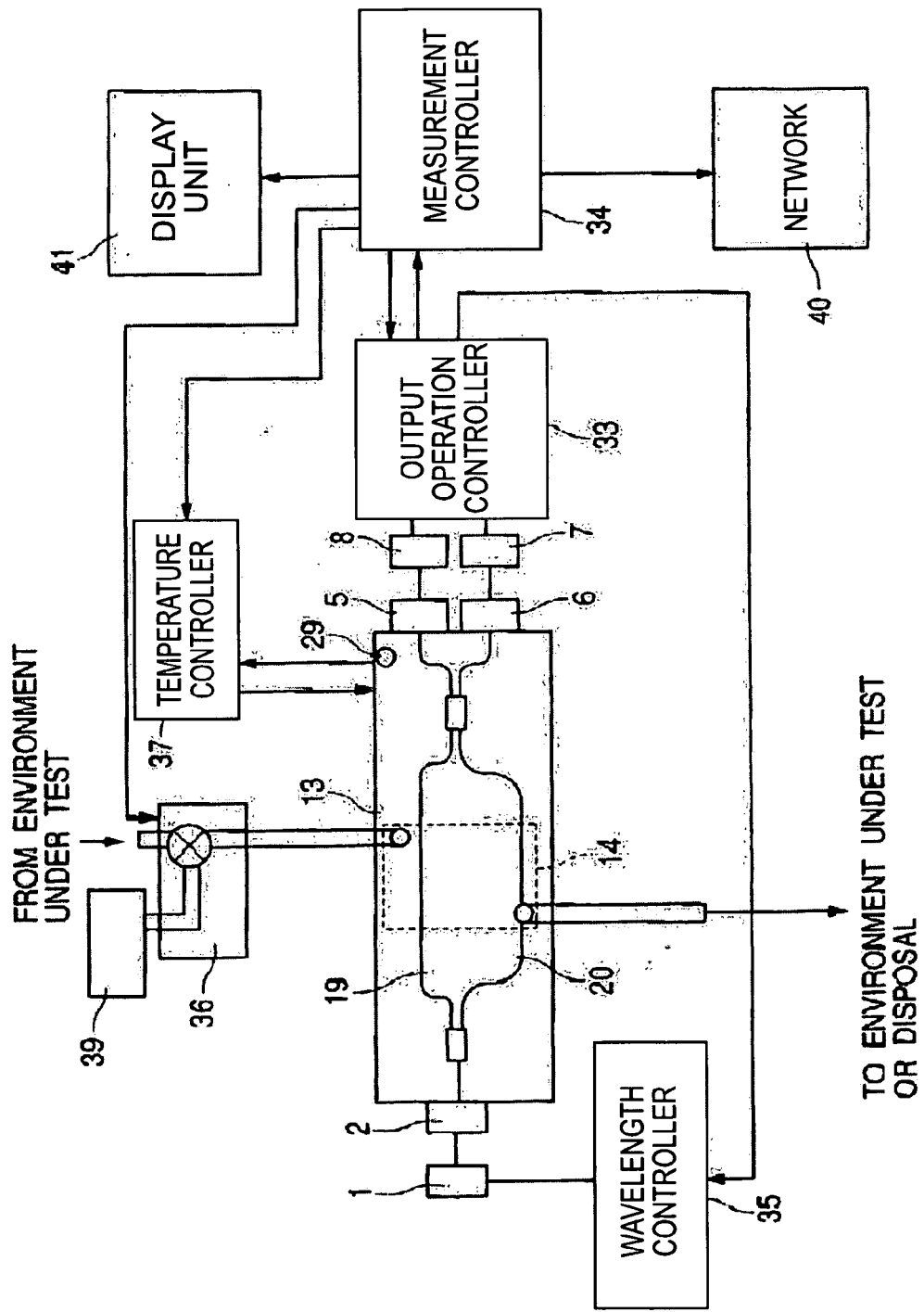
FIG. 9 is a block diagram showing the structure of a first embodiment of a chemical substance measuring apparatus of the present invention.

FIG. 9 is a block diagram showing the structure of a second embodiment of a chemical substance measuring apparatus in the present invention. This example is intended to measure the amount of dioxin in the environment under test, using the chemical substance detection sensor of the first embodiment. In the diagram of FIG. 9, components identical to those previously illustrated in FIG. 4 to FIG. 8 are assigned with same numerals and their detailed description is omitted. Likewise, in the following description of other examples, components identical to those previously illustrated are assigned with same numerals and their detailed description is omitted.

A tank 39 holds a solution (for example, pure water or reference sample) for comparison that does not contain the substance to be detected. The solution flows into the reaction chamber 14. This flow is controlled by the flow controller 36 which is operated from the measurement controller 34. The outputs of the photodetectors 8 and 7, which vary according to for example the temperature in the environment, are fed to the output operation controller 33. The output operation controller processes the outputs (PD1 and PD2) from the photodetectors 8 and 7, and then sends a signal to a wavelength controller 35 so that (PD1−PD2)/(PD1+PD2) becomes 0 (zero). The wavelength controller 35 controls the voltage or current applied to the light source (laser diode) 1 in order to control the wavelength of the light source 1 so the phase difference is set at the operating point.

Next, the flow controller 36 switches the flow so the sample from the environment under test (sample to be measured) flows into the reaction chamber 14. At this point, the wavelength of the light source 1 is maintained at the wavelength determined by the above-mentioned control. The (PD1−PD2)/(PD1+PD2) signal varies according to the concentration of the detected substance contained in the sample under test. This output signal is sent to the measurement controller 34 which determines the concentration of the detected substance by referring to calibration data obtained beforehand for converting the measurement data into the corresponding concentration of the detected substance, and then transmits the concentration data to a display unit 41 and other terminals on a network 40. Of course, in order to maintain the equilibrium during reaction between the substance to be detected 26 and the ligand 25, the temperatures of the substrate 13 and inside the reaction chamber 14 are maintained at constant levels by a temperature controller 37. The Peltier element 28 is used for this temperature control along with a thermistor 29 or a similar device for monitoring the temperature. The solution containing the substance to be detected (dioxin) is injected from the environment into the reaction chamber 14 via the input port 15 and is then returned to the original environment or disposed of through the output port 16.

As described above, the measurement controller 34 controls the flow controller 36, temperature controller 37, and output operation controller 33. The measurement controller 34 also displays measurement results on the display unit 41 and creates output data for the network. The output operation controller 33 generates a signal for controlling the wavelength controller 35 during setting of the operating point so that (PD1−PD2)/(PD1+PD2) reaches 0 (zero), and during measurement of the sample under test, maintains the control signal for the wavelength controller obtained at the time of setting the operating point.

(Third Embodiment)

Figure 10:
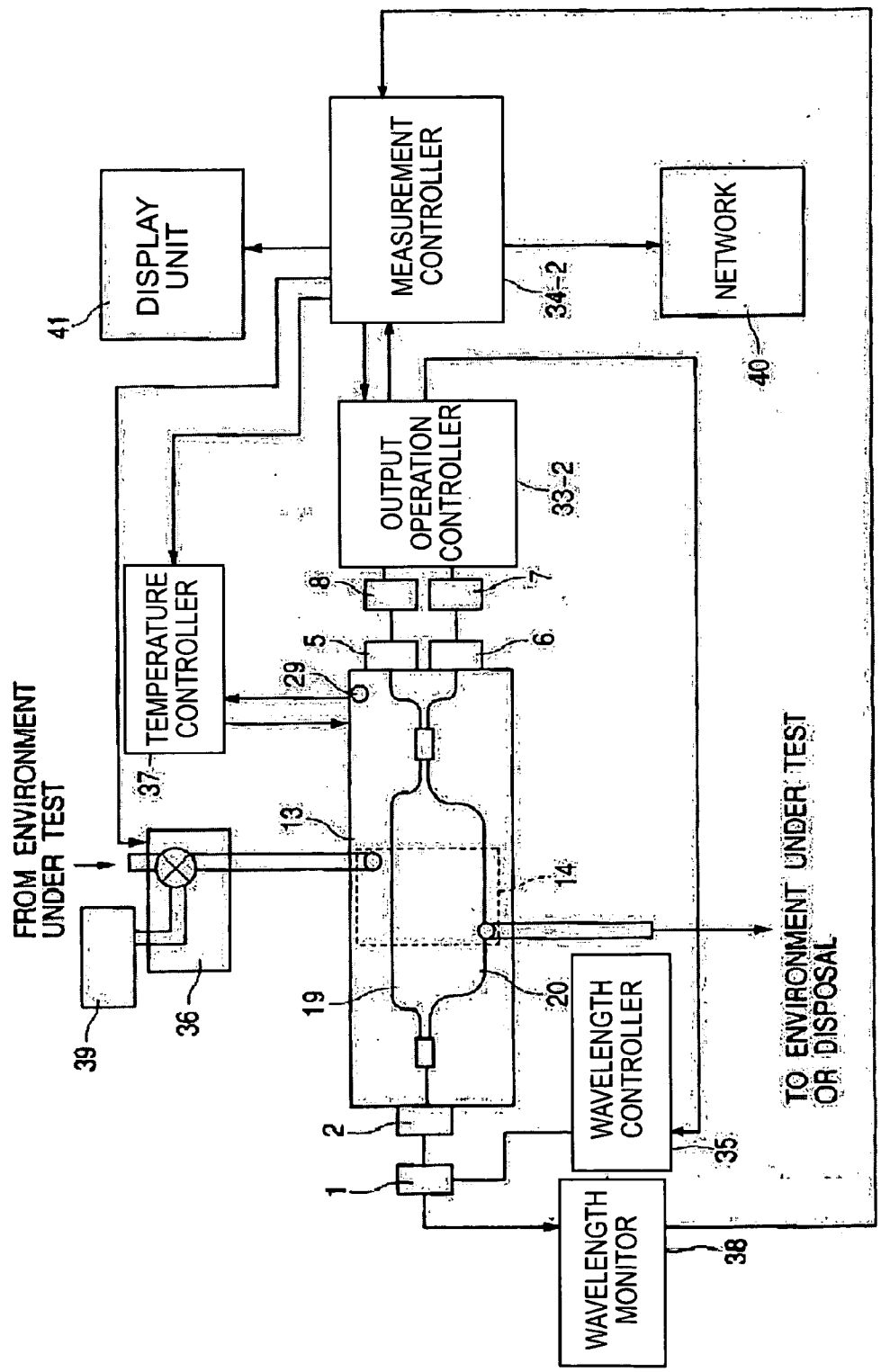
FIG. 10 is a block diagram showing the structure of a second embodiment of a chemical substance measuring apparatus of the present invention.

FIG. 10 is a block diagram showing the structure of a third embodiment of a chemical substance measuring apparatus in the present invention. The point differing from the embodiment shown in FIG. 9 is that a wavelength monitor 38 is installed for detecting the amount of change in the wavelength of the light source 1 between when the sample under test is measured and when the operating point is set, and then feeds it back to the measurement controller 34-2. This wavelength monitor 38 for detecting the amount of wavelength change monitors the temperature of the laser and converts it into a wavelength by utilizing the relation between the temperature and wavelength of the laser, or directly measures the wavelength of the light from the light source 1 by separating wavelengths with an etalon, or grating, etc.

As in the case of the example shown in FIG. 9, the apparatus of this embodiment uses the chemical substance detection sensor of the present invention, and functions as follows:

First of all, the wavelength is adjusted so that the light intensities being detected with the photodetectors 8 and 7 become equal when setting the operating point using the reference sample. In other words, the operating point is set when the reference sample to be detected is flowing from the tank 39 into the reaction chamber 14.

Next, the sample to be measured is guided from the environment under test into the reaction chamber 14, and the wavelength is changed so as to cancel out the phase change caused by adsorption to the ligand 25. More specifically, the wavelength of the wavelength-tunable light source 1 is adjusted by sending an appropriate signal to the wavelength controller 35, so that the light intensities being detected with the photodetectors 8 and 7 are kept balanced. The wavelength monitor 38 sends the wavelength change to the measurement controller 34-2. The measurement controller 34-2 calculates the amount of phase change from the amount of wavelength change by using the data (showing the correlation between the amount of phase change and the amount of wavelength change) acquired in advance. The measurement controller 34-2 further determines the concentration of the detected substance by converting the amount of phase change into the corresponding amount of the adsorbed substance to be detected and then outputs the concentration data to the display unit 41 and other terminals on the network 40.

As described above, the output operation controller 33-2 has a function to acquire a control signal for controlling the wavelength controller 35, so that its output becomes 0 (zero) during measurement of the reference sample (during setting of the operating point) and also during measurement of the sample under test. The measurement controller 34-2 has a function to convert the amount of phase change detected with the wavelength monitor 38, into the corresponding amount of the adsorbed substance to be detected, and then outputs the concentration data to the display unit 41 and terminals on the network.

The chemical substance measuring apparatus of this example provides significant improvements in accuracy for wavelength control and monitoring and is therefore capable of increasing the measurement sensitivity.

Furthermore, when changing the wavelength so as to equalize the light intensity entering the photodetectors 8 and 7, the accuracy for changing the wavelength can be enhanced by maximizing the differential amount of the output difference between the photodetectors 8 and 7. When the wavelength is periodically changed, the output difference between the photodetectors 8 and 7 is changed as well. The conditions under which the time differential of the difference in output between the photodetectors 8 and 7 is maximized are identical to the conditions under which the outputs of the photodetectors 8 and 7 are balanced. Accordingly, the wavelength can be controlled so as to equalize the outputs of the photodetectors 8 and 7, by using the condition that the time differential of the output difference between the photodetectors 8 and 7 is maximized.

In this example, the difference $\delta L$ in the length between the optical waveguides 19 and 20 is $(\frac{1}{4}) \cdot \lambda$ in order to enhance the measurement sensitivity. Here $\lambda$ is the wavelength propagating in the optical waveguides. Assuming that the lengths of the optical waveguides 19 and 20 are L and $\delta L$ respectively, and the amount of wavelength change is $\delta \lambda$ when the wavelength is changed to cancel out the phase change occurring as the substance to be detected is adsorbed to the optical waveguide substrate, then the relation between the change in the refractive $\delta n$ caused due to the detected substance and the amount of wavelength change $\delta \lambda$ will be $\delta n = \{\delta L/(\lambda \cdot L)\} \cdot \delta \lambda$. This relation shows that $\delta \lambda$ will be larger as the $\{\delta L/(\lambda \cdot L)\}$ value becomes smaller while the change in the refractive index $\delta n$ is low. In other words, the smaller the $\{\delta L/(\lambda \cdot L)\}$ value, the higher the sensitivity will be. Under the condition that the change in the intensity is most significant versus the phase change, the $\delta L/\lambda$ value will be minimized at $\delta L/\lambda = \frac{1}{4}$. It is obvious that sensitivity increases as the length L is extended, but the light loss also increases. Since the length L depends on the lower limit of the photodetector sensitivity, the optimal length should be determined while taking the photodetector sensitivity into account.

(Fourth Embodiment)

Figure 11:
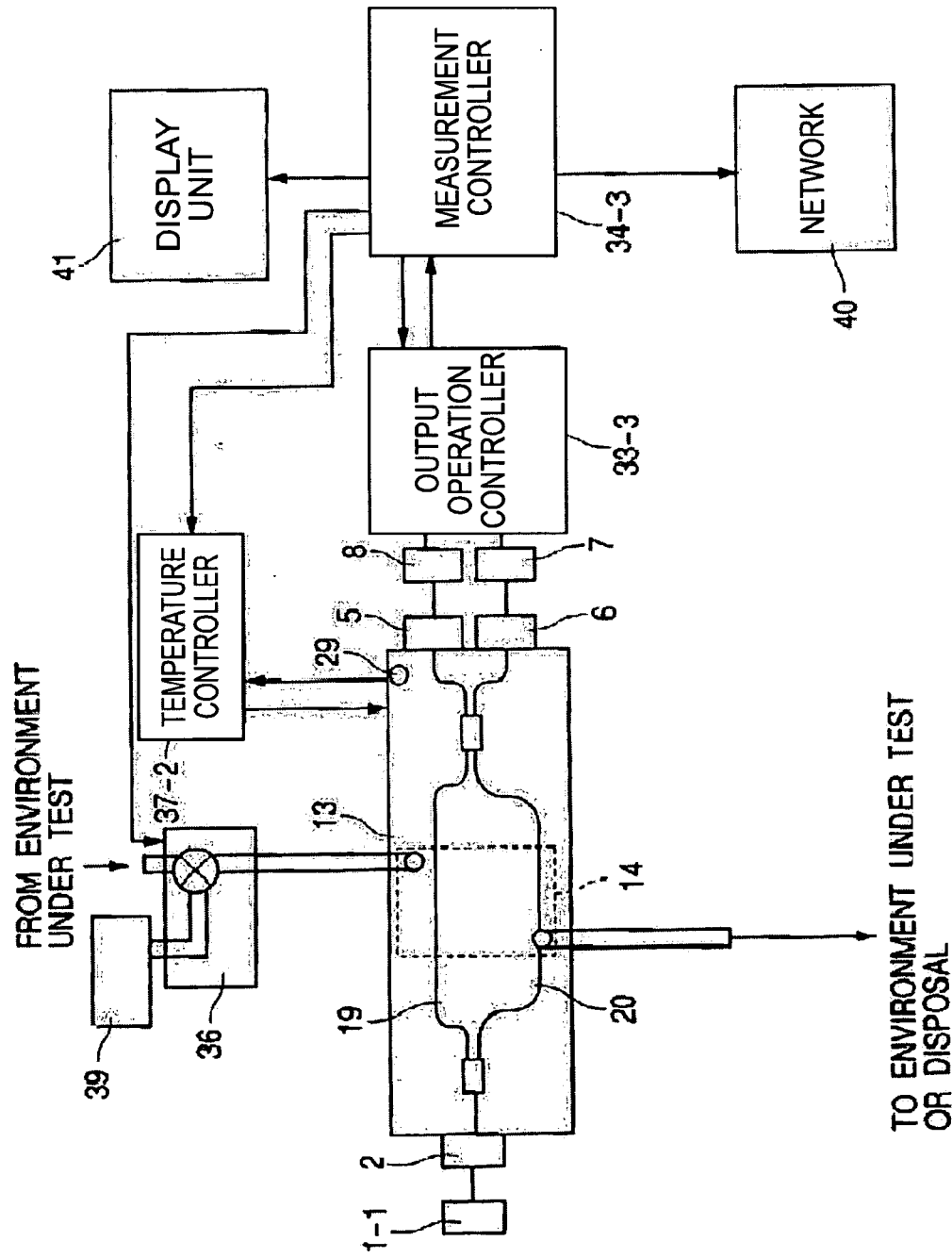
FIG. 11 is a block diagram showing the structure of a third embodiment of a chemical substance measuring apparatus of the present invention.

FIG. 11 is a block diagram showing the structure of a fourth example of a chemical substance measuring apparatus in the present invention. A point differing from the embodiment illustrated in FIG. 9 is that the light source 1-1 for the chemical substance detection sensor is comprised of a fixed-wavelength light source. Another difference from FIG. 9 is that the output operation controller 33-3, measurement controller 34-3, and temperature controller 37-2 are configured to equalize the intensities of the two light beams after they are combined and redivided, so that the intensity change versus the amount of phase change is maximized while controlling the temperature of at least one portion of the optical waveguide substrate 13.

During measurement of a chemical substance, as in the case of the previous example, the concentration of the chemical substance to be detected is output by directly measuring (PD1−PD2)/(PD1+PD2) or by measuring the substrate temperature at which (PD1−PD2)/(PD1+PD2) is 0 (zero). In this case, the data on the substrate temperature versus the concentration of the substance to be detected should be prepared beforehand, to determine the concentration of the substance from the detected temperature. This example has no bulk optics, requires no wavelength controller for the light source, and is capable of setting the operating point by controlling the temperature of at least one section of the substrate 13, making it easier to fabricate a measurement apparatus.

(Fifth Embodiment)

Figure 12:
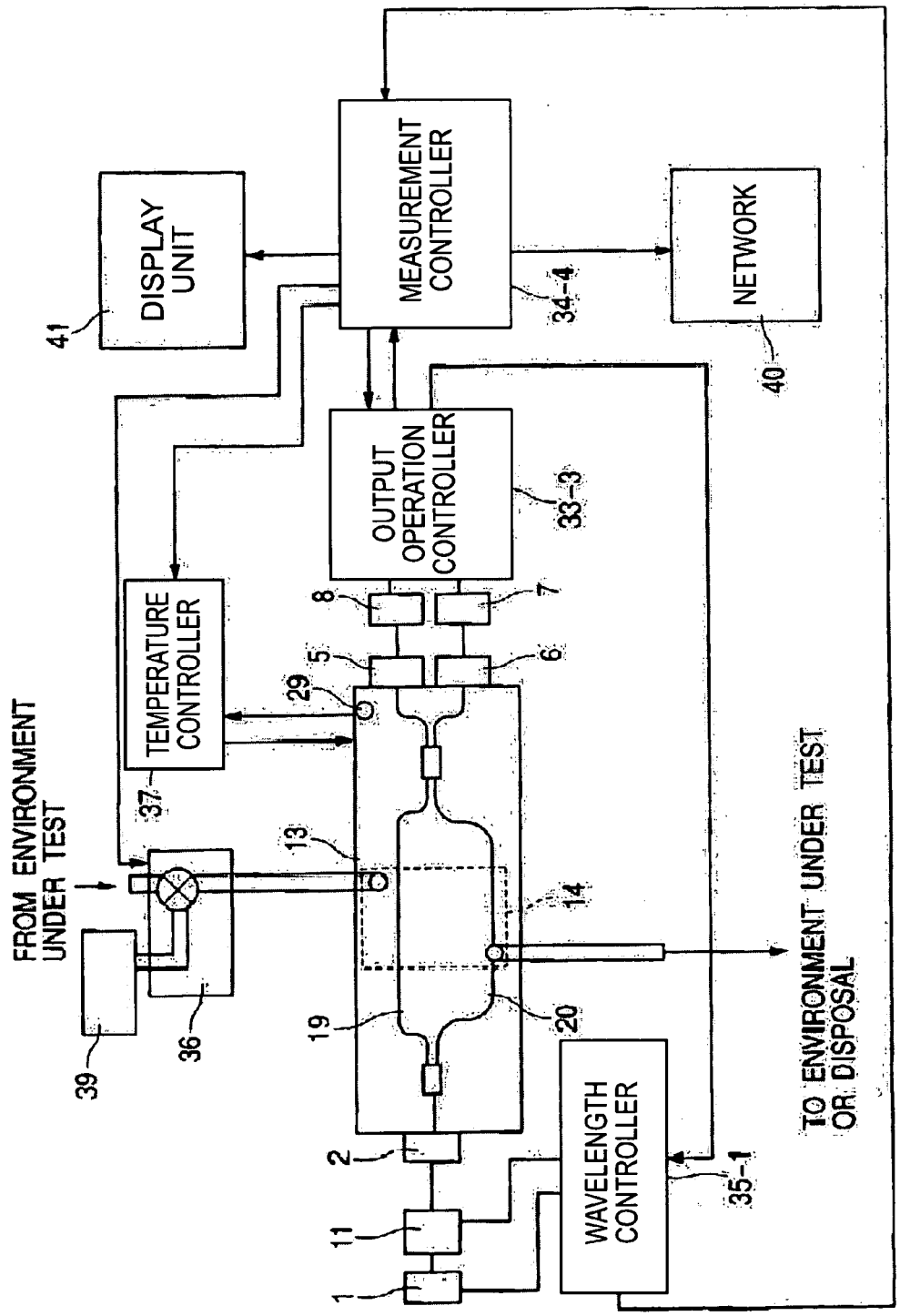
FIG. 12 is a block diagram showing the structure of a fourth embodiment of a chemical substance measuring apparatus of the present invention.

FIG. 12 is a block diagram showing the structure of a fifth embodiment of a chemical substance measuring apparatus in the present invention. This example simultaneously uses a light source having a wavelength-tunable function and an acousto-optic device 11 for wavelength conversion, in order to achieve very high sensitivity. The acousto-optic device 11 has acousto-optic effects that cause a wavelength shift when a high frequency wave is applied, to an extent equal to the applied frequency.

A point differing from the embodiment illustrated in FIG. 9 is that the acousto-optic device 11 is installed between the light source 1 and the optical coupler 2, and the wavelength of the light source 1 is controlled by the wavelength controller 35-1. In this embodiment, the same as in the embodiment shown in FIG. 9, the reference sample flows from the tank 39 into the reaction chamber 14, and the operating point is set by using the wavelength conversion function of the light source 1 so that PD1−PD2 reaches 0 (zero). Next, the sample under test containing the substance to be detected is supplied to the reaction chamber 14. At this point, the high frequency applied to the acousto-optic device 11 is shifted so as to maintain PD1−PD2=0. This frequency change is fed to the measurement controller 34-4 which then converts the frequency change into the concentration of the detected substance by referring to the correlation data on the frequency change versus the concentration that has been acquired in advance. If the concentration of the detected substance is high, it might exceed the upper limit of the high frequency applied to the acousto-optic device 11 from the wavelength controller 35-1. In this case, the frequency applied to the acousto-optic device 11 is reset to 0 (zero) and the wavelength is shifted to the extent equal to the frequency shift so that PD1−PD2=0 is maintained. At this point, the same signal as given to the wavelength-tunable light source is also output to the measurement controller 34-4 which converts that signal into a wavelength change and further converts it into the corresponding concentration to create the output data. The wavelength-tunable light source used in this example is a distributed feedback laser module incorporating a Peltier element and a thermistor. The laser temperature is constantly measured with the thermistor and a wavelength change is calculated by utilizing the fact that the laser oscillation wavelength has a temperature dependence of 0.1 nm/° C.

At this time when changing the wavelength to equalize the light intensities entering the photodetectors 8 and 7, the accuracy for changing the wavelength can be enhanced by maximizing the differential amount in output (PD1−PD2) between the photodetectors 8 and 7.

In this embodiment the temperature of the substrate 13 and inside the reaction chamber 14 is also controlled by the temperature controller 37. To reduce the change in the refractive index of the optical waveguides 19 and 20 due to the temperature change of the substrate 13, a glass substrate is used for the substrate 13. In this glass substrate, a clad layer is formed by $SiO_2$ doped with Ge to a depth of 10 microns, and the core layer is formed by Si3N4 with a refractive index of 1.9 and a film thickness of 0.2 microns. The width of the optical waveguides is 6 millimeters, the same as the first embodiment. The difference between the lengths of the optical waveguides 19 and 20 is 0.25 microns, which is ¼ of the wavelength. Using this structure, this example succeeded in improving sensitivity more than 2 orders of magnitude higher than the first embodiment of the chemical substance measuring apparatus in the present invention.

(Sixth Embodiment)

Figure 13:
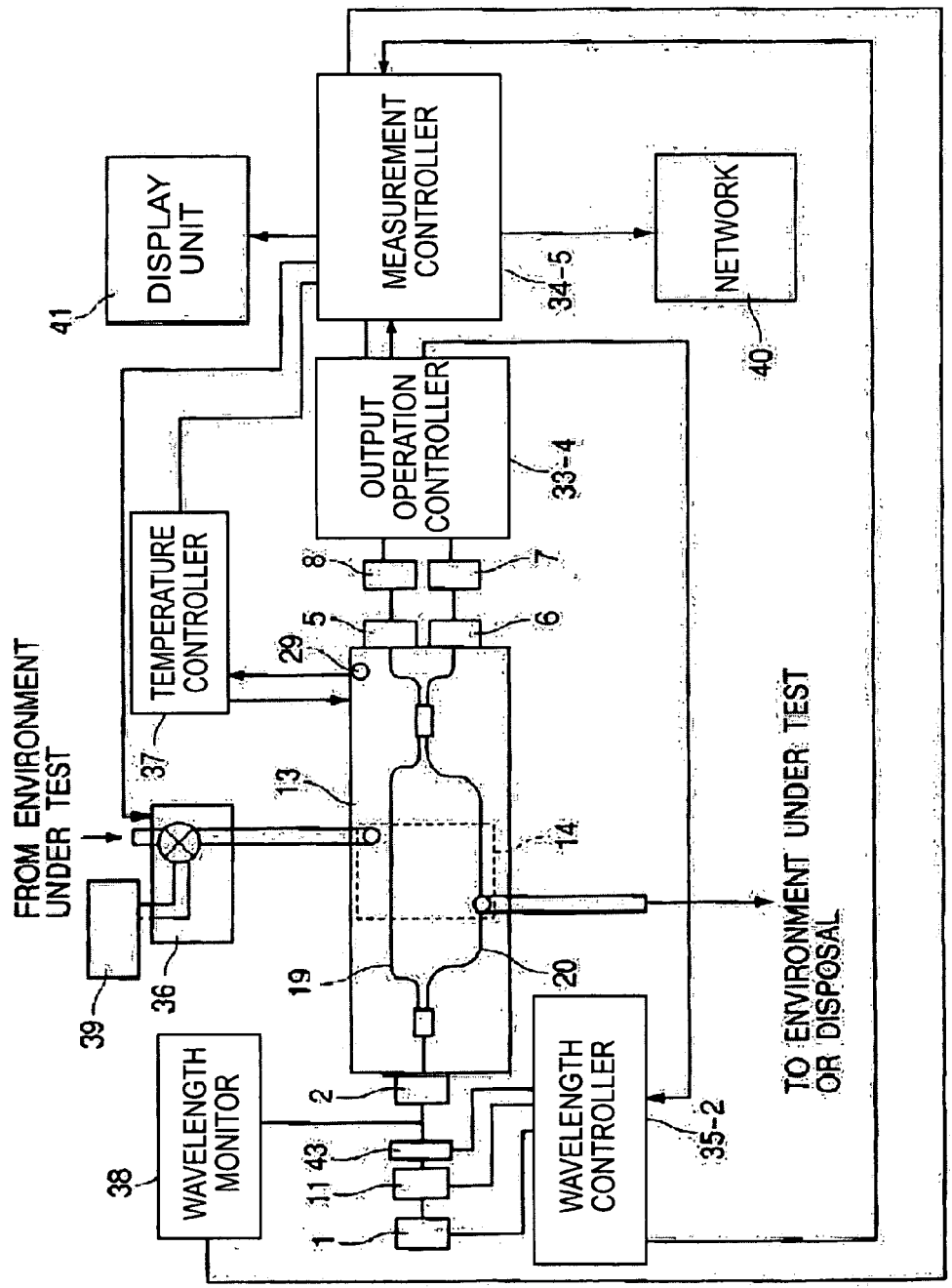
FIG. 13 is a block diagram showing the structure of a fifth embodiment of a chemical substance measuring apparatus of the present invention.

FIG. 13 is a block diagram showing the structure of a sixth embodiment of a chemical substance measuring apparatus in the present invention. This example provides an improvement of the embodiment illustrated in FIG. 12.

To monitor the wavelength change, this example uses a wavelength monitor 38 installed in conjunction with a device having an etalon or grating and a photodetector. The wavelength data measured with the wavelength monitor is fed back to the measurement controller 34-5. This delivers higher measurement accuracy than in the fifth embodiment of a chemical substance measuring apparatus wherein the temperature of the distributed feedback laser 1 is fed back to the measurement controller 34-4.

In addition, a phase modulator 11 utilizing electro-optic effects is used as a wavelength converter. This phase modulator generates wavelength-shifted light when a sine wave voltage is applied. To prevent the oscillation wavelength of the laser 1 from being applied to the optical waveguides at this point, a variable band-pass filter 43 is interposed between the phase modulator 11 and the optical coupler 2.

The chemical substance detection sensor of the present invention is capable of setting the optimal operating point by controlling the wavelength of the light source and/or controlling the temperature in the reaction chamber, without using bulk optics that require a mechanical movement means. A compact chemical substance detection sensor with excellent operation stability and high sensitivity can therefore be provided.

What is claimed is:

1. A chemical substance detection sensor for use with a sample comprising:
    two optical waveguides having different optical path lengths for dividing and transmitting light emitted and divided from a light source;
    a reaction chamber for allowing a sample to flow through regions of said two optical waveguides wherein ligands are provided on at least one of said two optical waveguides;
    an optical combiner for combining light outputs from said two optical waveguides; and
    a detector for detecting a chemical substance contained in said sample by capturing the interference light output from said optical combiner, wherein
    said sensor further comprises a wavelength-tuning device for adjusting the light wavelengths of said light source, wherein the optical path lengths of said two optical waveguides differ from each other by a ¼ wavelength or more.

2. A chemical substance detection sensor according to claim 1, wherein
said wavelength-tuning device is a wavelength-tunable semiconductor laser.

3. A chemical substance detection sensor according to claim 1, wherein
said wavelength-tuning device is comprised of a converter for converting light wavelengths generated from a fixed-wavelength light source.

4. A chemical substance detection sensor according to claim 3, wherein
an acousto-optic device is installed between said light source and said two optical waveguides.

5. A chemical substance detection sensor as in claim 1
wherein said sensor includes a temperature controller for said reaction chamber, and the optical path lengths of said two optical waveguides differ from each other by ¼ or more wavelength.

6. A chemical substance measuring apparatus for use with a sample comprising:
two optical waveguides having different path length for dividing and transmitting light emitted from a light source;
a reaction chamber for allowing a sample to flow through regions of said two optical waveguides wherein ligands are provided on at least one of said two optical waveguides;
an optical combiner/splitter for combining and redividing outputs from said two optical waveguides;
an output operation controller for measuring a chemical substance contained in said sample based on interference light output from said optical combiner/splitter;
a flow controller for controlling a flow of the sample into said reaction chamber;
a temperature controller for controlling the temperature in said reaction chamber; and
a measurement controller coupled to said output operation controller, for control of at least said flow controller and temperature controller, wherein
said apparatus further comprises a wavelength-tunable device for adjusting wavelengths of light of said light source, wherein the optical path lengths of said two optical waveguides differ from each other by ¼ or more wavelength, and said wavelength-tunable device is configured to adjust the wavelengths of light of said light source so that the intensities of two interference outputs from said optical combiner/splitter are equalized when a reference sample flows in said reaction chamber and said adjusted wavelength of said light source is maintained while a test sample flows in said reaction chamber.

7. A chemical substance measuring apparatus according to claim 6, wherein
said wavelength-tunable device for adjusting the light wavelengths of said light source comprises a wavelength-tunable semiconductor laser having a voltage control for said wavelength-tunable semiconductor laser.

8. A chemical substance measuring apparatus according to claim 6, wherein
said wavelength-tunable device for adjusting the light wavelengths of said light source is comprised of a fixed-wavelength light source and a wavelength conversion device for converting fixed wavelength output light of said light source.

9. A chemical substance measuring apparatus according to claim 8, wherein
a wavelength monitor device is installed on the output side of said wavelength-tunable device which adjusts fixed-wavelength output light of said light source, and which monitors changes in the light wavelength adjusted by said wavelength-tunable device and which feeds the data on said light wavelength changes back to said measurement controller.

10. A chemical substance measuring apparatus according to claim 8, wherein
said wavelength converter device is a phase modulator possessing electro-optic effects wherein said apparatus further comprises a signal generator for applying a sinusoidal wave to said phase modulator, and also a filter for blocking unmodulated wavelength components of fixed-wavelength light from said light source installed between said phase modulator and said optical waveguides.

11. A chemical substance measuring apparatus as in claim 6 comprising:
wherein said light source is a fixed-wavelength light source, and the optical path lengths of said two optical waveguides differ from each other by ¼ or more wavelengths, and said temperature controller and said measurement controller are configured to set a temperature at which the intensities of the two interference outputs from said optical combiner/splitter are equalized when the reference sample flows in said reaction chamber and also to maintain the temperature in said reaction chamber at said temperature level while the sample under test flows in said reaction chamber.

12. A chemical substance measuring apparatus for use with a sample comprising:
at least one chemical substance detection sensor having a reaction chamber for the sample and optical waveguides having different path lengths running through the reaction chamber;
an output operation controller for measuring a chemical substance contained in the sample based on output of the chemical substance detection sensor;
a flow controller for controlling flow of the sample into said reaction chamber;
a temperature controller for controlling the temperature in said reaction chamber;
a measurement controller coupled to said output operation controller, for control of at least said flow controller and said temperature controller, wherein
said temperature controller, said flow controller, and said measurement controller are configured to set a temperature level at which the intensities of two interference outputs from an optical combiner/splitter are equalized when a reference sample flows in said reaction chamber and also to determine the operating point where the temperature level is maintained in said reaction chamber while the sample under test flows in said reaction chamber.

13. The chemical substance detection sensor for use with a sample of claim 1 wherein:
the ligands are antigens.

14. The chemical substance detection sensor for use with a sample of claim 1 wherein:
the ligands are antibodies.

15. The chemical substance detection sensor for use with a sample of claim 1 wherein:
the ligands are DNA.

16. The chemical substance detection sensor for use with a sample of claim 1 wherein:
the ligands are RNA.

17. The chemical substance detection sensor for use with a sample of claim 1 wherein:
the reaction chamber and the ligands are arranged to detect antigens.

18. The chemical substance detection sensor for use with a sample of claim 1 wherein:
the reaction chamber and the ligands are arranged to detect antibodies.

19. The chemical substance detection sensor for use with a sample of claim 1 wherein:
the reaction chamber and the ligands are arranged to detect DNA.

20. The chemical substance detection sensor for use with a sample of claim 1 wherein:
the reaction chamber and the ligands are arranged to detect RNA.

* * * * *